United States Patent
Laufer et al.

(10) Patent No.: US 10,351,652 B2
(45) Date of Patent: Jul. 16, 2019

(54) METHOD FOR THE SYNTHESIS OF POLYMER CARBODIIMIDES WITH ADDED CESIUM SALTS, POLYMER CARBODIIMIDES, AND USE THEREOF

(71) Applicant: LANXESS Deutschland GmbH, Cologne (DE)

(72) Inventors: Wilhelm Laufer, Ellerstadt (DE); Oliver Herd, Wuppertal (DE); Rolf Sperber, Wuppertal (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 15/735,295

(22) PCT Filed: Jun. 14, 2016

(86) PCT No.: PCT/EP2016/063601
§ 371 (c)(1),
(2) Date: Dec. 11, 2017

(87) PCT Pub. No.: WO2016/202781
PCT Pub. Date: Dec. 22, 2016

(65) Prior Publication Data
US 2018/0171058 A1    Jun. 21, 2018

(30) Foreign Application Priority Data
Jun. 15, 2015  (EP) .................................. 15172169

(51) Int. Cl.
| | |
|---|---|
| *C08G 18/00* | (2006.01) |
| *C08G 61/04* | (2006.01) |
| *C08G 18/02* | (2006.01) |
| *C07C 267/00* | (2006.01) |
| *C08K 5/29* | (2006.01) |
| *C08G 18/48* | (2006.01) |
| *C08G 18/76* | (2006.01) |
| *C08G 18/22* | (2006.01) |
| *C08G 18/42* | (2006.01) |
| *C09J 175/06* | (2006.01) |
| *C08G 18/75* | (2006.01) |
| *C08G 18/79* | (2006.01) |

(52) U.S. Cl.
CPC .......... *C08G 18/025* (2013.01); *C07C 267/00* (2013.01); *C08G 18/225* (2013.01); *C08G 18/42* (2013.01); *C08G 18/4236* (2013.01); *C08G 18/4833* (2013.01); *C08G 18/755* (2013.01); *C08G 18/7671* (2013.01); *C08G 18/792* (2013.01); *C08K 5/29* (2013.01); *C09J 175/06* (2013.01); *C08G 2105/06* (2013.01); *C08G 2170/20* (2013.01)

(58) Field of Classification Search
CPC .. C08G 18/025; C08G 2170/20; C08G 18/42; C08G 18/7671; C08G 18/225; C08G 2105/06; C08G 18/4833; C08G 18/797; C08G 18/4236; C09J 175/06; C09J 175/04; C08K 5/29; C08L 75/04
USPC .......................................... 528/80, 44; 520/1
See application file for complete search history.

(56) References Cited

U.S. PATENT DOCUMENTS

| | | | | |
|---|---|---|---|---|
| 5,360,933 | A | * 11/1994 | Imashiro | ............... C07C 265/08 528/67 |
| 5,498,747 | A | 3/1996 | Pohl et al. | |
| 5,597,942 | A | 1/1997 | Pohl et al. | |
| 5,912,290 | A | * 6/1999 | Imashiro | ............... C08G 18/71 524/195 |
| 6,602,926 | B1 | * 8/2003 | Heiliger | ............... C08G 18/283 502/174 |
| 9,512,299 | B2 | 12/2016 | Laufer et al. | |
| 2005/0085616 | A1 | * 4/2005 | Licht | ....................... C04B 24/28 528/61 |
| 2007/0208158 | A1 | 9/2007 | Kramer | |
| 2017/0088509 | A1 | * 3/2017 | Laufer | .................. C07C 267/00 |

OTHER PUBLICATIONS

Neumann, W. et al., "The Preparation of Carbodiimides from Isocyanates", Angew, Chem. Internat. Edit, vol. 1 (1962), No. 12, pp. 621-625.
Wagner, K., et al, "a, w-Diisocyanato-carbodiimide und-polycarbodiimide sowie ihre Derivate", 1981, Angew. Chem. 93, Issue 10, available at http://onlinelibrary.wiley.com, pp. 855-866, Abstract, five pages.
European Search Report from corresponding European Application No. 15172169, dated Oct. 21, 2015, two pages.

* cited by examiner

*Primary Examiner* — Jessica Whiteley

(57) ABSTRACT

The present invention relates to processes for producing polymeric carbodiimides by addition of cesium salts and to polymeric carbodiimides produced by this process and to the use thereof as a hydrolysis inhibitor, especially in polyurethane (PU)-based systems, preferably thermoplastic TPU, PU adhesives, PU casting resins, PU elastomers or PU foams.

14 Claims, No Drawings

METHOD FOR THE SYNTHESIS OF POLYMER CARBODIIMIDES WITH ADDED CESIUM SALTS, POLYMER CARBODIIMIDES, AND USE THEREOF

The present invention relates to processes for producing polymeric carbodiimides, to the polymeric carbodiimides produced by this process and to the use thereof as a hydrolysis inhibitor in polyurethane (PU)-based systems, preferably thermoplastic TPU, PU adhesives, PU casting resins, PU elastomers or PU foams.

Carbodiimides have proven useful in many applications, for example as hydrolysis inhibitors for thermoplastics, ester-based polyols, polyurethanes, triglycerides and lubricating oils etc.

In the prior art the synthesis of carbodiimides proceeds from isocyanates which are carbodiimidized under basic or heterocyclic catalysis to eliminate $CO_2$. This allows mono- or polyfunctional isocyanates to be converted into monomeric or polymeric carbodiimides.

Typically used catalysts are alkali metal or alkaline earth metal compounds, for example alkali metal alkoxides and heterocyclic compounds containing phosphorus, as described for example in the publication Angewandte Chemie, see Angew. Chem. 1962, 74, 801-806 and Angew. Chem. 1981, 93, 855-866.

The production of sterically hindered polymeric carbodiimides according to the prior art succeeds only with the aid of phosphorus-containing catalysts (for example phospholenes). Complete removal of these phosphorus-containing catalysts is technically not possible. Since carbodiimides are preferably employed in the production of polyurethanes, the presence of phosphorus, even in trace amounts, is extremely disruptive and is therefore to be avoided.

The present invention accordingly has for its object to provide an improved process allowing production of polymeric carbodiimides in high yield and moreover polymeric carbodiimides that are free from organic phosphorus compounds and may therefore be employed in the production and/or stabilization of PU systems.

It has now been found that, surprisingly, the abovementioned objects are achieved when polymeric carbodiimides are converted (carbodiimidized) by conversion of isocyanate-containing compounds in the presence of at least one basic cesium salt at temperatures between 120° C. to 220° C., preferably 160° C. to 200° C., very particularly preferably 180° C. to 200° C.

The present invention accordingly provides a process for producing polymeric carbodiimides of formula (I)

$$R^1—R^2—(—N=C=N—R^2—)_m—R^1 \quad (1),$$

in which
m represents an integer from 2 to 500, preferably 3 to 20, very particularly preferably 4 to 10,
$R^2=C_1$-$C_{18}$-alkylene, $C_5$-$C_{18}$-cycloalkylene, arylene, $C_7$-$C_{18}$-alkylarylene and/or $C_7$-$C_{18}$-aralkylene, preferably alkylarylene and/or $C_7$-$C_{18}$-aralkylene
and
$R^1=$—NCO, —$NCNR^2$, —$NHCONHR^4$, —$NHCONR^4R^5$ or —$NHCOOR^6$,
wherein in $R^1$ independently of one another $R^4$ and $R^5$ are identical or different and represent a $C_1$-$C_6$-alkyl, $C_6$-$C_{10}$-cycloalkyl or $C_7$-$C_{18}$-aralkyl radical and $R^6$ has one of the definitions of $R^1$ or represents a polyester or a polyamide radical or —$(CH_2)_h$—O—$[(CH_2)_k$—O$]_g$—$R^7$,
where h=1-3, k=1-3, g=0-12 and
$R^7$=H or $C_1$-$C_4$-alkyl, whereby isocyanate-containing compounds of formula (II)

$$O=C=N—R^2—R^1 \quad (II)$$

optionally in the presence of isocyanate-containing compounds of formula (III)

$$O=C=N—R^2 \quad (III),$$

wherein $R^2$ and $R^1$ are as defined above,
are converted (carbodiimidized) in the presence of at least one basic cesium salt at temperatures between 120° C. to 220° C., preferably 160° C. to 200° C., very particularly preferably 180° C. to 200° C.

In the context of the invention the basic cesium salts employed are preferably cesium carbonate and/or cesium alkoxides, preferably cesium methoxide.

The basic cesium salts are preferably employed in a concentration of 0.1 to 20 wt %, particularly preferably 1 to 5 wt %, very particularly preferably 2 to 4 wt %.

Particularly preferred isocyanate-containing compounds of formula (II) are the compounds recited hereinbelow which are employed individually or in the combinations recited hereinbelow:
(IIa), (IIb), (IIc) or (IId) alone or (IIa) and (IIb) together, wherein these compounds correspond to the formulae

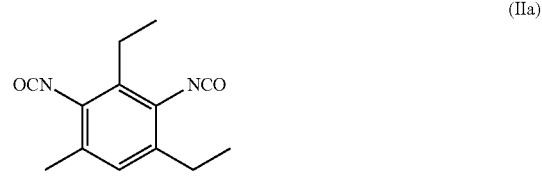

(IIa)

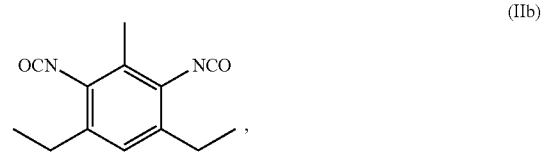

(IIb)

(IIc)

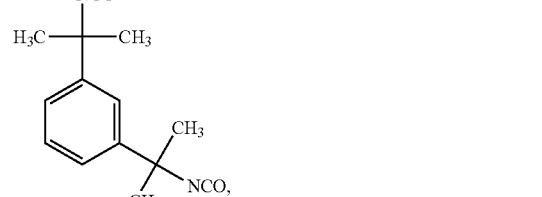

(IId)

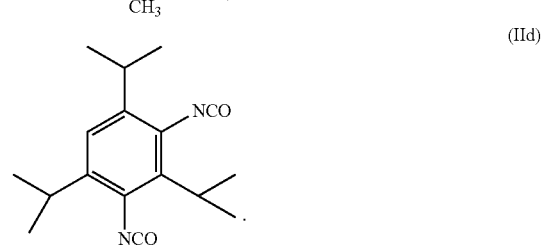

These compounds of formula (III) are preferably dl- and/or triisopropylphenyl isocyanate and isopropenyldimethylbenzyl isocyanate.

In a preferred embodiment of the process according to the invention following the carbodiimidization the basic cesium salts are filtered off and/or removed by extraction using a solvent, preferably water and/or alcohol.

The carbodiimidization may be performed either in the absence or in the presence of a solvent. Preferably employed solvents are $C_7$-$C_{22}$-alkylbenzenes, paraffin oils, polyethylene glycol dimethyl ethers, ketones or lactones.

When the reaction mixture has the desired content of NCO groups, corresponding to an average degree of condensation of m=2 to 500, preferably 3 to 20, very particularly preferably 4 to 10, the polycarbodiimidization is preferably terminated.

In one embodiment of the present invention the temperature of the reaction mixture is to this end reduced to 50° C.-120° C., preferably 60° C.-100° C., particularly preferably to 80° C.-90° C., and the basic cesium salts are removed by filtration or extraction. In a preferred production variant of the carbodiimides according to the invention the excess isocyanate-containing compounds are subsequently distilled off at temperatures of 150° C.-200° C., preferably 160° C.-180° C.

In a further embodiment of the present invention the free terminal isocyanate groups of the carbodiimides are subsequently reacted with aliphatic and/or aromatic amines, alcohols and/or alkoxypolyoxyalkylene alcohols, preferably in a slight excess of —NH, —NH$_2$ and/or —OH groups, optionally in the presence of a PU catalyst known to a person skilled in the art, preferably tert. amines or organotin compounds, particularly preferably DBTL (dibutyltin dilaurate) or DOTL (dioctyltin dilaurate). The amount of substance ratio of amines, alcohols and/or alkoxypolyoxyalkylene alcohols to carbodiimides of formula (I) is preferably 1.005-1.05:1, particularly preferably 1.01-1.03:1, based on the N=C=O groups present.

In a further embodiment of the present invention to interrupt the carbodiimidization the temperature of the reaction mixture is reduced to 50-120° C., preferably 60-100° C., particularly preferably to 80-90° C. and optionally after addition of a solvent, preferably selected from the group of $C_7$-$C_{22}$-alkylbenzenes, particularly preferably toluene, the free terminal isocyanate groups of the carbodiimides are reacted with aliphatic and/or aromatic amines, alcohols and/or alkoxypolyoxyalkylene alcohols, preferably in a slight excess of —NH, —NH$_2$ and/or —OH groups, optionally in the presence of a PU catalyst known to one skilled the art, preferably tert. amines or organotin compounds, particularly preferably DBTL (dibutyltin dilaurate) or DOTL (dioctyltin dilaurate). The amount of substance ratio of amines, alcohols and/or alkoxypolyoxyalkylene alcohols to carbodiimides of formula (I) is preferably 1.005-1.05:1, particularly preferably 1.01-1.03:1, based on the N=C=O groups present.

In a further embodiment of the invention the production of the inventive polymeric carbodiimides of formula (I) is effected via a partial, by preference <50%, preferably <40%, end-functionalization of the free NCO groups in the isocyanate-containing compounds of formula (I) where $R^1$=—NCO with primary or secondary amines or alcohols and/or alkoxypolyoxyalkylene alcohols in the diisocyanates and subsequent carbodiimidization to eliminate carbon dioxide at temperatures of 80° C. to 200° C. in the presence of cesium salts and optionally solvent.

The carbodiimides according to the invention are preferably purified after production thereof. The crude products may be purified by distillation and/or by solvent extraction. Suitable solvents for purification which may be used with preference are $C_7$-$C_{22}$-akylbenzenes, paraffin oils, alcohols, ketones or esters. These are commodity solvents.

The present invention further provides polymeric carbodiimides of formula (I) obtainable by the process according to the invention.

The present invention further provides stabilizers containing at least 90% of polymeric carbodiimides of formula (I), preferably obtainable by the process according to the invention, comprising a proportion of less than 1 ppm of organic phosphorus compounds, such as preferably phospholene oxides.

In a further preferred embodiment of the invention the stabilizers according to the invention by preference comprise not more than 1000 ppm, preferably not more than 100 ppm and particularly preferably not more than 10 ppm of cesium salts.

The stabilizers especially allow exceptional hydrolysis protection.

The present invention further provides processes for producing polyurethanes (PU), preferably thermoplastic polyurethanes, whereby the reaction of the polyols, preferably the polyester polyols, with the isocyanates is performed in the presence of the polymeric carbodiimides according to the invention and/or the polymeric carbodiimides according to the invention are added to the polyurethane following the reaction.

In a further preferred embodiment of the invention the process is performed in the presence of PU catalysts and auxiliary and/or additive substances.

The production of the polyurethanes is preferably effected such as is described in WO 2005/111136 A1.

Polyurethanes are formed virtually quantitatively by polyaddition reaction of polyisocyanates with polyhydric alcohols, the polyols, preferably polyester polyols. Linkage is effected by the reaction of an isocyanate group (—N=C=O) of one molecule with a hydroxyl group (—OH) of another molecule to form a urethane group (—NH—CO—O—).

The profile of the reaction between diisocyanate and polyol is dependent on the molar ratio of the components. Intermediates having a desired average molecular weight and desired end groups may readily be obtained. These intermediates may then be reacted (chain-extended) with a diol or diamine at a later juncture to then form the desired polyurethane or polyurethane-polyurea hybrid. The intermediates are generally referred to as prepolymers.

Suitable polyols for the production of prepolymers are polyalkylene glycol ethers, polyether esters or polyesters having terminal hydroxyl groups (polyester polyols).

The polyols in the context of the invention are compounds by preference having a molecular weight in (g/mol) of up to 2000, preferably in the range from 500 to 2000 and particularly preferably in the range from 500 to 1000.

The term "polyol" in the context of the invention encompasses both diols and triols, and also compounds having more than three hydroxyl groups per molecule. The use of triols is particularly preferred.

Preferred polyols are polyester polyols and/or polyether ester polyols.

It is advantageous when the polyol has an OH number of up to 200, preferably between 20 and 150 and particularly preferably between 50 and 115.

Especially suitable are polyester polyols being reaction products of various polyols with aromatic or aliphatic dicarboxylic acids and/or polymers of lactones.

Preference is given here to aromatic dicarboxylic acids which may be used for forming suitable polyester polyols. Particular preference is given here to terephthalic acid, isophthalic acid, phthalic acid, phthalic anhydride and substituted dicarboxylic acid compounds having a benzene ring.

Preferred aliphatic dicarboxylic acids are those that may be used for forming suitable polyester polyols, particularly preferably sebacic acid, adipic acid and glutaric acid.

Preferred polymers of lactones are those that may be used for forming suitable polyester polyols, particularly preferably polycaprolactone.

Both the dicarboxylic acids and the polymers of lactones are commodity chemicals.

Particular preference is also given to polyols that may be used for forming suitable polyester polyols, very particularly preferably ethylene glycol, butanediol, neopentyl glycol, hexanediol, propylene glycol, dipropylene glycol, diethylene glycol and cyclohexanedimethanol.

In a further preferred embodiment of the invention, the polyols are polyether ester polyols.

Preferred therefor are the reaction products of various aforementioned polyols with aromatic or aliphatic dicarboxylic acids and/or polymers of lactones (e.g. polycaprolactone).

The polyols employed in the context of the inventions are commodity chemicals obtainable from Bayer MaterialScience AG under the trade names Baycoll® and Desmophen®.

Preferred diisocyanates are aromatic and aliphatic diisocyanates. Particular preference is given to toluene 2,4-diisocyanate, toluene 2,6-diisocyanate, phenylene diisocyanate, 4,4-diphenylmethane diisocyanate, methylenebis(4-phenyl isocyanate), naphthalene 1,5-diisocyanate, tetramethylene 1,4-diisocyanate and/or hexamethylene 1,6-diisocyanate, very particular preference to toluene 2,4-diisocyanate and toluene 2,6-diisocyanate.

The diisocyanates employed in the context of the inventions are commodity chemicals obtainable for example from Bayer MaterialScience AG under the trade name Desmodur®.

In a further embodiment of the invention, the composition additionally comprises at least one diamine and/or diol.

Preferred diamines employed for the chain extension are 2-methylpropyl 3,5-diamino-4-chlorobenzoate, bis(4,4'-amino-3-chlorophenyl)methane, 3,5-dimethylthio-2,4-tolylenediamine, 3,5-dimethylthio-2,4-tolylenediamine, 3,5-diethyl-2,4-tolylenediamine, 3,5-diethyl-2,6-tolylenediamine, 4,4'-methylenebis(3-chloro-2,6-diethylaniline) and 1,3-propanediol bis(4-aminobenzoate).

Preferred diols are butanediol, neopentyl glycol, hexanediol, propylene glycol, dipropylene glycol, diethylene glycol and/or cyclohexanedimethanol.

The diamines or diols employed in the context of the invention for chain extension are commodity chemicals available from Rheinchemie Rheinau GmbH under the trade name Addolink®.

Catalysts employed are preferably dibutyltin dilaurates or triethylenediamine in dipropylene glycol.

The catalysts used in the context of the inventions are commodity chemicals available from Rheinchemie Rheinau GmbH under the Addocat® trade name.

In a particularly preferred embodiment of the present invention the inventive polymeric carbodiimide of formula (I) is employed in an amount of 0.1 to 2 wt %, preferably 0.5 to 1.5 wt %, particularly preferably 1.0 to 1.5 wt %, based on the overall mixture.

The present invention further provides for the use of the inventive polymeric carbodiimide of formula (I) in processes for producing polyurethanes as a hydrolysis stabilizer.

The polyurethane (PU)-based systems produced by this process feature excellent stability to hydrolysis.

The present invention further provides for the use of the inventive polymeric carbodiimide of formula (I) for hydrolysis protection, preferably in polyurethanes.

The purview of the invention encompasses all hereinabove and hereinbelow recited general or preferred definitions of radicals, indices, parameters and elucidations among themselves, i.e. including between the respective ranges and preferences in any desired combination.

The examples which follow serve to elucidate the invention but have no limiting effect.

EXEMPLARY EMBODIMENTS

Example 1

Production of a polymeric carbodiimide by reaction of the compound of formula (IIc) with cesium carbonate (inventive).

Example 2

Production of a polymeric carbodiimide by reaction of the compound of formula (IIc) with potassium methoxide (comparative).

Example 3

Production of a polymeric carbodiimide by reaction of the compound of formula (IIc) with potassium carbonate (comparative).

Example 4

Production of a polymeric carbodiimide by reaction of the compound of formula (IIc) with sodium carbonate (comparative).

Example 5

Production of a polymeric carbodiimide by reaction of the compound of formula (IIc) phospholene oxide (comparative).

General Production Procedure for Examples 1-5

30 g of the isocyanate-containing compound of formula (IIc) were weighed into a 100 mL three-necked flask equipped with an internal thermometer, a reflux cooler and a protective gas inlet and subsequently for examples 1 to 4 0.9 g (3 wt %) and for example 5 0.03 g (0.1 wt %) of the respective catalyst according to table 1 were added. During the heating phase a light argon stream was passed over the vapor phase. The protective gas was turned off on commencement of $CO_2$ evolution. The mixture was allowed to stir vigorously for 3 h at 190° C. (example 1 and 5) or 12 h at 190° C. (example 2) or 6 h at 190° C. (examples 3 and 4) and the reaction mixture, once cooled to about 100° C., was subsequently filtered.

TABLE 1

Carbodiimide synthesis yields

| Example | Catalyst | T [° C.] | Duration [h] | Carbodiimide | Isocyanate | Byproducts |
|---|---|---|---|---|---|---|
| 1 | cesium carbonate | 190 | 3 | >98% | <1.0% | <1.0% |
| 2 | K-methoxide | 190 | 12 | <60% | >30% | >5.0% |
| 3 | potassium carbonate | 190 | 6 | <1% | 99% | n.d. |
| 4 | sodium carbonate | 190 | 6 | 0% | 100% | — |
| 5 | phospholene oxide | 190 | 3 | >95% | <1.0% | >1.0% |

Surprisingly, the cesium carbonate shows a high catalyst activity for the carbodiimidization and resulted in yields of over 98% after only 3 hours of reaction time and is accordingly markedly better than the synthesis via K methoxide or K or Na carbonate.

In addition the inventive catalyst may be removed simply by filtration whereas in the case of catalysis by a phosphorus-containing catalyst (methylphospholene oxide) a costly and complex distillation under vacuum must be performed to effect removal.

Production of Ester-Based PU Hotmelts and Characterization Thereof

Example 6

A hotmelt based on linear copolyester having primary hydroxyl functions and an average molecular weight of 3500 g/mol (Dynacoll® 7360) was produced and additized as per the following table:

Carbodiimides employed were:

(A) 2 wt % of polymeric carbodiimide of formula (I) where m=4-5 and $R^1$=—NHCOOR$^6$, wherein $R^6$ is a polyethylene glycol radical, produced by catalysis with cesium carbonate (inventive, as per example 1 but end-functionalized with polyethylene glycol), and

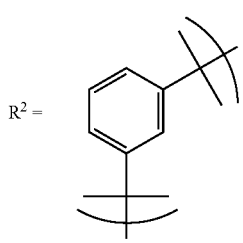

$R^2 =$

Characterization: no organic phosphorus compound detectable (<1 ppm phosphorus)

(B) 2 wt % of polymeric carbodiimide of formula (I) where m=4-5 and $R^1$=—NHCOOR$^6$, wherein $R^6$ is a polyethylene glycol article, produced by catalysis with methylphospholene oxide (comparative, see also process from WO-A 2005/111136), and

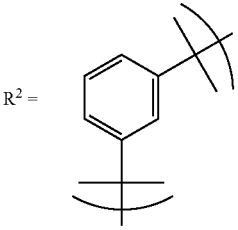

$R^2 =$

Characterization: residues of phosphorus detectable.

All reported quantities are in wt % based on the overall mixture.

The hotmelt was produced as follows:

The linear copolyester having primary hydroxyl functions was initially evacuated for 30 minutes at 120° C. This was followed by addition of 11.67 wt % of diphenylmethane diisocyanate (MDI) based on the overall formulation and the mixture was reacted for 60 minutes at 120° C. to afford the polyurethane adhesive.

The respective carbodiimides reported in table 2 additives were then incorporated into the hotmelt and an exposure time to the additives of 1 hour was ensured.

The thus produced and additized hotmelts were subjected to thermoageing at 130° C. for 48 hours in a cartridge. The hotmelt was filled into an aluminium cartridge (light- and moisture-tight) and aged in a circulating air oven for 48 hours at 130° C.

The samples was visually evaluated after ageing.

The results of the measurements are compiled in table 2:

TABLE 2

| Carbodiimide | Characterization |
|---|---|
| Example 6A (inv.) | No foam formation, very little bubble formation, if any, |
| Example 6B (C) | Foam/severe bubble formation |

(C) = comparative example;
(inv.) = inventive

SUMMARY

These tests show that use of the phosphorus-free carbodiimide according to the invention does not result in any appreciable disruptive side effects in terms of foaming. On the contrary, carbodiimides catalyzed with phospholene oxide and still containing traces of organophosphorus compounds exhibit the reported disadvantages of foam formation.

What is claimed is:

1. A process for producing polymeric carbodiimides of formula (I)

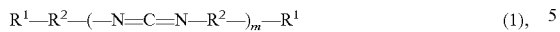

in which:

m represents an integer from 2 to 500, $R^2 = C_1\text{-}C_{18}$-alkylene, $C_5\text{-}C_{18}$-cycloalkylene, arylene, $C_7\text{-}C_{18}$ alkylarylene and/or $C_7\text{-}C_{18}$-aralkylene, and $R^1 = -NCO$, $NCNR^2$, $NHCONHR^4$, $-NHCONHR^2$, $-NHCONR^4R^5$ or $-NHCOOR^6$, wherein in $R^1$:

independently of one another, $R^4$ and $R^5$ are identical or different and represent a $C_1\text{-}C_6$-alkyl, $C_6\text{-}C_{10}$-cycloalkyl or $C_7\text{-}C_{18}$-aralkyl radical, and $R^6$ has one of the definitions of $R^1$ or represents a polyester or a polyamide radical or $-(CH_2)_h-O-[(CH_2)_k-O]_g-R^7$, where:

h=1-3, k=1-3, g=0-12; and $R^7$=H or $C_1\text{-}C_4$-alkyl, the process comprising carbodiimidizing isocyanate-containing compounds of formula (II)

optionally in the presence of isocyanate-containing compounds of formula (III)

wherein $R^1$ and $R^2$ are as defined above, in the presence of at least one basic cesium salt, and at a temperature of 120° C. to 220° C.

2. The process as claimed in claim 1, wherein the basic cesium salt is cesium carbonate and/or cesium alkoxide.

3. The process as claimed in claim 1, wherein the isocyanate-containing compounds of formula (II) comprise:

any of (IIa), (IIb), (IIc) or (IId) alone, or (IIa) and (IIb) together, wherein these compounds correspond to the following formulae

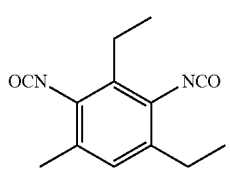

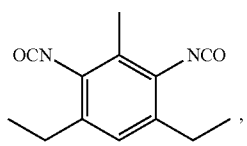

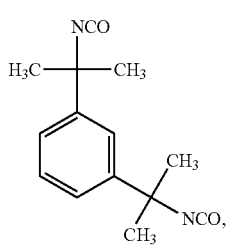

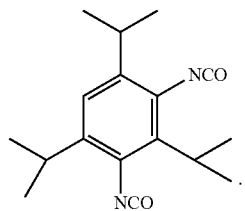

4. The process according to claim 1, wherein the basic cesium salt is employed in a concentration of 0.1 to 20 wt %, based on the overall mixture.

5. The process according to claim 1, further comprising, following the carbodiimidization, filtering off and/or removing the basic cesium salts by extraction using a solvent.

6. The process as claimed in claim 1, further comprising conducting the carbodiimidization in the presence of a solvent.

7. The process according to claim 6, wherein the solvent comprises at least one $C_7\text{-}C_{22}$-alkylbenzene.

8. A Stabilizer comprising at least 90% of the polymeric carbodiimides according to claim 1 and less than 1 ppm of organic phosphorus compounds.

9. A process for producing polyurethanes, the process comprising one of:

reacting polyester polyols with isocyanates in the presence of the polymeric carbodiimides produced according to claim 1, or reacting polyester polyols with isocyanates, and following the reaction, adding the polymeric carbodiimides produced according to claim 1.

10. The process according to claim 9, wherein the polymeric carbodiimide is employed in an amount of 0.1 to 2 wt %.

11. The process according to claim 9, wherein the polymeric carbodiimide is employed in an amount of 1.0 to 1.5 wt %, based on the overall mixture.

12. The process as claimed in claim 1, wherein:

m represents an integer from 3 to 20;

$R^2 = C_7\text{-}C_{18}$ alkylarylene and/or $C_7\text{-}C_{18}$-aralkylene; and the temperature is 160° C. to 200° C.

13. The process as claimed in claim 12, wherein:

m represents an integer from 4 to 10;

the isocyanate-containing compounds of formula (II) comprise:

any of (IIa), (IIb), (IIc) or (IId) alone, or (IIa) and (IIb) together, wherein these compounds correspond to the following formulae

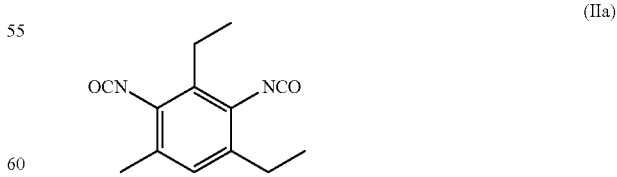

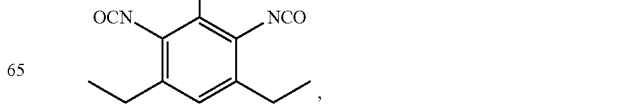

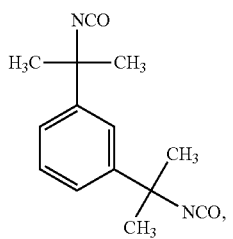

(IIc)

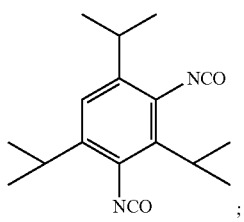

(IId)

and
- the basic cesium salt is employed in a concentration of 0.1 to 20 wt %, based on the overall mixture.

14. The process as claimed in claim 1, wherein:
- the basic cesium salt is cesium methoxide, and the basic cesium salt is employed in a concentration of 2 to 4 wt %, based on the overall mixture; and
- the isocyanate-containing compounds of formula (II) are converted in the presence of the isocyanate-containing compounds of formula (III) at a temperature of 180° C. to 200° C.

* * * * *